US008137690B2

(12) United States Patent
Hitzig

(10) Patent No.: US 8,137,690 B2
(45) Date of Patent: Mar. 20, 2012

(54) TASTE TITRATION THERAPIES

(75) Inventor: Pietr Hitzig, Rosedale, MD (US)

(73) Assignee: Health Innovations, LLC, Placerville, CA (US)

( * ) Notice: Subject to any disclaimer, the term of this patent is extended or adjusted under 35 U.S.C. 154(b) by 126 days.

(21) Appl. No.: 12/355,632

(22) Filed: Jan. 16, 2009

(65) Prior Publication Data

US 2009/0186935 A1    Jul. 23, 2009

Related U.S. Application Data

(60) Provisional application No. 61/011,369, filed on Jan. 17, 2008.

(51) Int. Cl.
*A61K 47/00* (2006.01)

(52) U.S. Cl. ........................................ 424/439

(58) Field of Classification Search .................. None
See application file for complete search history.

(56) References Cited

U.S. PATENT DOCUMENTS

| | | | | |
|---|---|---|---|---|
| 5,502,080 A * | 3/1996 | Hitzig | ............................ | 514/654 |
| 5,534,552 A * | 7/1996 | Bapat | ............................ | 514/667 |
| 5,658,955 A * | 8/1997 | Hitzig | ............................ | 514/654 |
| 5,776,493 A | 7/1998 | Barclay et al. | | |
| 6,264,981 B1 | 7/2001 | Zhang et al. | | |
| 2006/0034873 A1 * | 2/2006 | Radke et al. | .................. | 424/400 |

FOREIGN PATENT DOCUMENTS

WO    WO 94/21244    9/1994

OTHER PUBLICATIONS

International Preliminary Report on Patentability for PCT/US2009/000326, Jul. 23, 2010, Hitzig, et al.
International Search Report for PCT/US2009/000326, Sep. 1, 2009, Hitzig, et al.
Arad, G., et al., Broad-Spectrum Immunity Against Superantigens is Elicited in Mice Protected from Lethal Shock by a Superantigen Antagonist Peptide, *Immunology Letters*, 91(2-3), Feb. 15, 2004, 141-145.
Arzt, E.S., et al., Immunomodulation by Indoleamines: Serotonin and Melatonin Action on DNA and Interferon-Gamma Synthesis by Human Peripheral Blood Mononuclear Cells, *J Clin Immunol*, Nov. 1988, 8(6), 513-520.
Arzt, E, et al., Serotonin Inhibition of Tumor Necrosis Factor-Alpha Synthesis by Human Moncytes, *Life Sci*, 1991, 48(26), 2557-2562.
Azmitia, E.F., Modern Views on an Ancient Chemical: Serotonin Effects on Cell Proliferation, Maturation, and Apoptosis, *Brain Research Bulletin*, 2001, 56(5), 413-424.
Azmitia, E.C., Serotonin Neurons, Neuroplasticity, and Homeostasis of Neural Tissue, *Neuropsychopharmacology*, 1999, 21(2S), 33S-45S.
Beck, G.C., et al., Clinical Review: Immunomodulatory Effects of Dopamine in General Inflammation, *Crit Care*, 2004, 8(6), 485-491.
Bergman, J., Medications for Stimulant Abuse: Agonist-based Strategies and Preclinical Evaluation of the Mixed-action D-sub-2 Partial Agonist Aripiprazole (Abilify®), *Exp Clin Psychopharmacol*, Dec. 2008, 16(6), 475-483.
Berridge, K.C., The Debate Over Dopamine's Role in Reward: The Case for Incentive Salience, *Psychopharmacology* (Berl), Apr. 2007, 191(3), 391-431.
Beutler, B., et al., Passive Immunization Against Cachectin/Tumor Necrosis Factor Protects Mice from Lethal Effects of Endotoxin, *Science*, Aug. 30, 1985, 229(4716), 869-871.
Bielekova, B., et al., Therapeutic Potential of Phosphodiesterase-4 and -3 Inhibitors in Th1-Mediated Autolmmune Diseases, *J Immunol*, Jan. 15, 2000, 164(2), 1117-1124.
Bienvenu, J., et al., Production of Proinflammatory Cytokines and Cytokines Involved in the TH1/TH2 Balance is Modulated by Pentoxifylline, *J Cardiovasc Pharmacol*, 1995, 25(Suppl 2), S80-S84.
Birdsall, T.C., 5-Hydroxytryptophan: A Clinically-Effective Serotonin Precursor, *Alternative Medicine Review*, 1998, 3(4), 271-280.
Bonney, E.A., et al., Much IDO About Pregnancy, *Nature Medicine*, Oct. 1998, 4(10), 1128-1129.
Brodie, B., et al., A Concept for a Role of Serotonin and Noepinephrine as Chemical Mediators in the Brain, *Ann N Y Acad Sci.*, Mar. 14, 1957, 66(3), 631-642.
Brown, R.R., et al., Implications of Interferon-Induced Tryptophan Catabolism in Cancer, Auto-Immune Diseases and AIDS, *Adv Exp Med Biol.*, 1991, 294, 425-435.
Butler, J.L., et al., Anti-IL-12 and Anti-TNF Antibodies Synergistically Suppress the Progression of Murine Collagen-Induced Arthritis, *Eur J Immunol*, 1999, 29, 2205-2212.

(Continued)

*Primary Examiner* — Anand Desai
*Assistant Examiner* — Melissa Mercier
(74) *Attorney, Agent, or Firm* — Syndicated Law; Brian S. Boyer

(57) ABSTRACT

The teachings provided herein generally relate to formulations, systems, and methods that have the ability to remit deficiencies and imbalances in a subject's serotonin and dopamine levels. The teachings relate to the preparation and uses of a formulation comprising a serotonergic agent or dopaminergic agent in a form capable of oral transmucosal delivery to a subject. The formulation includes a flavoring agent and a carrier base. The flavoring agent functions as a taste indicator of the endpoint of a taste titration of the serotonergic or dopaminergic agent for a subject receiving an oral administration of the formulation in the form of a taste titration, and the endpoint is indicated to the subject by a change in the intensity of the flavor of the flavoring agent.

54 Claims, No Drawings

OTHER PUBLICATIONS

Caine, S. B., et al., Effects of Dopamine $D_{1\text{-}like}$ and $D_{2\text{-}like}$ Agonists in Rats That Self-Administer Cocaine[1], *The Journal of Pharmacology and Experimental Therapeutics*, 1999, 291, 353-360.

Calcinaro, F., et al., Protection from Autoimmune Diabetes by Adjuvant Therapy in the Non-Obese Diabetic Mouse: The Role of Interleukin-4 and Interleukin-10, *Immunol Cell Biol*, 1997, 75, 467-471.

Canete, J.D., et al., Differential Th1/Th2 Cytokine Patterns in Chronic Arthritis: Interferon γ is Highly Expressed in Synovium of Rheumatoid Arthritis Compared With Seronegative Spondyloarthropathies, *Ann Rheum Dis*, 2000, 59, 263-268.

Carr, L., et al., The Enhancement of T Cell Proliferation by L-Dopa is Mediated Peripherally and Does Not Involve Interleukin-2, *J Neuroimmunol*, Sep. 2003, 142(1-2), 166-169.

Carson, M.K., et al., A Rose by Any Other Name? The Potential Consequences of Microglial Heterogeneity During CNS Health and Disease, *Neurotherapeutics*, Oct. 2007, 4(4), 571-579.

Cenci, E, et al., Induction of Protective Th1 Responses to Candida Albicans by Antifungal Therapy Alone or in Comination With an Interleukin-4 Antagonist, *J Infect Dis*, Jul. 1997, 176(1), 217-226.

Chaitidis, P., et,al., Th2 Response of Human Peripheral Monocytes Involves Isoform-Specific Induction of Monoamine Oxidase-A[1,2], *The Journal of Immunology*, 2004, 173, 4821-4827.

Chen, J., et al., Chronic Stimulation of D1 Dopamine Receptors in Human SK-N-MC Neuroblastoma Cells Induces Nitric-Oxide Synthase Activation and Cytotoxicity, *J Biol Chem*, Jul. 25, 2003, 278(30), 28089-28100.

Ciccocioppo, R., The Role of Serotonin in Craving: From Basic Research to Human Studies, *Alcohol Alcohol*, Mar.-Apr. 1999, 34(2), 224-53.

Clerici, M., et al., A $T_H1 \rightarrow T_H2$ Switch is a Critical Step in the Etiology of HIV Infection, *Immunology Today*, 1993, 14(3), 107-111.

Connor, T.J., et al., An Assessment of the Acute Effects of the Serotonin Releasers Methylenedioxymethamphetamine, Methylenedioxyamphetamine and Fenfluramine on Immunity in Rats, *Immunopharmacology*, Mar. 2000, 46(3), 223-235.

Culmsee, C., et al., p53 in Neuronal Apoptosis, *Biochem Biophys Res Commun.*, Jun. 10, 2005, 331(3), 761-777.

Dabbagh, K., et al., Toll-Like Receptors and T-Helper-1/T-Helper-2 Responses, *Curr Opin Infect Dis*, 2003, 16, 199-204.

Daw, N.D., et al., Opponent Interactions Between Serotonin and Dopamine, *Neural Netw.*, Jun.-Jul. 2002, 15(4-6), 603-616.

Derogatis, L.R., SCL-90-R® (Symposium Checklist-09-Revised), 2008, Pearson Education, Inc. [online] [retrieved on Apr. 28, 2010] URL: http://psychcorp.pearsonassessments.com/HAIWEB/Cultures/en-us/Productdetail.htm?Pid=PAg514.

Devoiko, L.V., et al., Analysis of the Interaction of the Dopaminergic and Serotoninergic Systems in Immunomodulation, *Fiziol Zh SSSR Im I M Sechenova*, Feb. 1984, 70(2), 239-246.

Di Chiara, G., Alcohol and Dopamine, *Alcohol Health Res World*, 1997, 21(2), 108-114 [online] [retrieved on May 11, 2010] URL: http://pubs.niaaa.nih.gov/publications/arh21-2/108.pdf.

Di Giovanni, G., et al., Serotonin/Dopamine Interaction—Focus on $5\text{-}HT_{2C}$ Receptor a New Target of Psychotropic Drugs, *Indian J Exp Biol.*, Dec. 2002, 40, 1344-1352.

Duan, W., et al., Paroxetine Retards Disease Onset and Progression in Huntingtin Mutant Mice, *Ann Neurol*, Apr. 2004, 55(4), 590-594.

Dumont, F.J., CTLA4-Ig Fusion Proteins: Promise for Improved Therapy of Transplant Rejection and Autoimmune Diseases, *Therapy*, Nov. 2004, 1(2), 289-304.

Ericson, M., et al., The Smoking Cessation Medication Varenicline Attenuates Alcohol and Nicotine Interactions in the Rat Mesolimbic Dopamine System, *J Pharmacol Exp Ther*, Jan. 6, 2009, 329(1), 225-230.

Fallarino, F., et al., T Cell Apoptosis by Tryptophan Catabolism, *Cell Death and Differentiation*, 2002, 9, 1069-1077.

Figueroa, F.E., et al., Bromocriptine Induces Immunological Changes Related to Disease Parameters in Rheumatoid Arthritis, *Br J Rehumatol*, Sep. 1997, 36(9) 1022-1027.

Fine, S.M., et al. Tumor Necrosis Factor a Inhibits Glutamate Uptake by Primary Human Astrocytes: Implications For Pathogenesis of HIV-1 Dementia, *The Journal of Biological Chemistry*, Jun. 28, 1996, 271, 15303-15306 [online] [retrieved Apr. 28, 2010] URL: http://www.jbc.org/content/271/26/15303.long.

Finnegan, A., et al., Proteoglycan (Aggrecan)-Induced Arthritis in BALB/c Mice is a Th1-Type Disease Regulated by Th2 Cytokines, *J. Immunol*, 1999, 163, 5383-5390.

Fletcher, P.J., et al., Serotonin Receptors as Potential Targets for Modulation of Nicotine Use and Dependence, *Prog Brain Res*, 2008, 172, 361-383.

Fletcher, P.J., et al., The $5\text{-}HT_{2C}$ Receptor Agonist Ro60-0175 Reduces Cocaine Self-Administration and Reinstatement Induced by the Stressor Yohimbine, and Contextual Cues, *Neuropsychopharmacology*, 2008, 33, 1402-1412.

Fletcher, P.J., et al., Injection of the 5-HT2C Receptor Agonist Ro60-0175 into the Ventral Tegmental Area Reduces Cocaine-Induced Locomotor Activity and Cocaine Self-Administration, *Neuropsychopharmacology*, Feb. 2004, 29(2), 308-318.

Franken, I.H., et al., The Role of Dopamine in Human Addition: from Reward to Motivated Attention, *Eur J Pharmacol*, Dec. 5, 2005, 526(1-3), 199-206.

Fujihira, K., et al., Suppression and Acceleration of Autoimmune Diabetes by Neutralization of Endogenous Interleukin-12 in NOD Mice, *Diabetes*, Dec. 2000, 49(12), 1998-2006.

Giacomelli, R., et al., Serum Levels of Soluble CD30 are increased in Ulcerative Colitis (UC) but not in Crohn's Disease (CD), *Clin Exp Immunol*, 1998, 111, 532-535.

Gouin, J-P., et al., Immune Dysregulation and Chronic Stress Among Older Adults: A Review, *Neuroimmunomodulation*, 2008, 15(4-6), 251-259.

Greiner, A., et al., Low-Grade B Cell Lymphomas of Mucosa-Associated Lymphoid Tissue (MALT-type) Require CD40-Mediated Signaling and Th2-Type Cytokines for In Vitro Growth and Differentiation, *Am J Pathol*, May 1997, 150(5), 1583-1593.

Grohmann, U., et al., IL-9 Protects Mice from Gram-Negative Bacterial Shock: Suppression of TNF-{alpha}, IL-12, and IFN-{gamma}, and Induction of IL-10, *J Immunol*, Apr. 15, 2000, 164(8), 4197-4203.

Grohmann, U., et al., Tolerance, DCs and Tryptophan: Much Ado About IDO, *Trends Immunol.*, May 2003, 24(5), 242-248.

Gursel, I., et al., Repetitive Elements in Mammalian Telomeres Suppress Bacterial DNA-Induced Immune Activation, *J Immunol.*, Aug. 2003, 171(3), 1393-1400.

Harada, K., et al., In Situ Nucleic Acid Hybridization of Cytokines in Primary Biliary Cirrhosis: Predominance of the Th1 Subset, *Hepatology*, Apr. 1997, 25(4), 791-796.

Hasko, G., et al., IL-12 as a Therapeutic Target for Pharmacological Modulation in Immune-Mediated and Inflammatory Diseases: Regulation of T Helper 1/T Helper 2 Responses, *Br J Pharmacol*, Jul. 1999, 137(6), 1295-1304.

Heath, T.P., et al., Human Taste Thresholds are Modulated by Serotonin and Noradrenaline, *J Neurosci.*, Dec. 6, 2006, 26(49), 12664-12671.

Hermann, H., et al., Coexpression of the Cannabinoid Receptor Type 1 With Dopamine and Serotonin Receptors in Distinct Neuronal Subpopulations of the Adult Mouse Forebrain, *Neuroscience*, 2002, 109(3), 451-460.

Hitzig, P., Combined Dopamine and Serotonin Agonists: A Synergistic Approach to Alcoholism and Other Addictive Behaviors, *MD Med J.*, Feb. 1993, 42(2) 153-157.

Hitzig, P., Combined Serotonin and Dopamine Indirect Agonists Correct Alcohol Craving and Alcohol-Associated Neuroses, *Journal of Substance Abuse Treatment*, 1994, 11(5), p. 489-490.

Hoebe, K. et al., The Interface Between Innate and Adaptive Immunity, *Nature Immunology*, 2004, 5(10), 971-974.

Howell, L.L., Nonhuman Primate Neuroimaging and Cocaine Medication Development, *Exp Clin Psychopharmacol*, Dec. 2008, 16(6): 446-57.

Idzko, M., et al., The Serotoninergic Receptors of Human Dendritic Cells: Identification and Coupling to Cytokine Release[1], *The Journal of Immunology*, 2004, 172, 6011-6019.

Ilani, T., et al., Dopaminergic Regulation of Immune Cells Via $D_3$ Dopamine Receptor: A Pathway Mediated by Activated T Cells, *FASEB J*, Oct. 2004, 18(13), 1600-1602.

Inoue, A., et al., Suppressive Effect on Theiler's Murine Encephalomyelities Virus-Induced Demyelinating Disease byt the Administration of Anti-IL-12 Antibody, *The Journal of Immunology*, 1998, 161, 5586-5593.

Joyce, J.N., et al., Neuroprotective Effects of the Novel $D_3/D_2$ Receptor Agonist and Antiparkinson Agent, S32504, In Vitro Against 1-Methyl-4-Phenylpyridinium (MPP+) and In Vivo Against 1-Methyl-4-Phenyl-1,2,3,6-Tetrahydropyridine (MPTP): A Comparison to Ropinirole, *Exp Neurol.*, Nov. 2003, 184(1), 393-407.

Kampman K.M.,et al., Combination of the Dopaminergic Agent, Phentermine, and the Serotonergic Agent, Fenfluramine, in the Treatment of Cocaine Dependence, *Journal of Substance Abuse Treatment*, Jul.-Aug. 1997, 14(4), p. 401-402.

Klein, T.W., et al., The Cannabinoid System and Immune Modulation, *J Leukoc Biol.*, Oct. 2003, 74(4), 486-496.

Kubera, M., et al., Effects of Serotonin and Serotonergic Agonists and Antagonists on the Production of Interferon-γ and Interleukin-10, *Neuropsychopharmacology*, 2000, 23(1), 89-98.

Kubera, M., et al., Effects of Serotonin and Serotonergic Agonists and Antagonists on the Production of Tumor Necrosis Factor a and Interleukin-6, *Psychiatry Res*, Apr. 30, 2005, 134(3), 251-258.

Lam, K.S.L., et al., Neurochemical Correlates of Autistic Disorder: A Review of the Literature, *Res Dev Disabil*, May-Jun. 2006, 27(3) 254-289.

Lambe, E.K., et al., Translational Studies on Glutamate and Dopamine Neurocircuitry in Addictions: Implications for Addiction Treatment, *Neuropsychopharmacology*, Jan. 2009, 34(2):255-256.

Le Foll, B., et al., Baseline Expression of Alpha4beta2* Nicotinic Acetylcholine Receptors Predicts Motivation to Self-administer Nicotine, *Bio Psychiatry*, Dec. 16, 2008, 65(8), 714-716.

Levitan, R.D., The Chronobiology and Neurobiology of Winter Seasonal Affective Disorder, *Dialogues Clin Neurosci*, 2007, 9(3), 315-324.

Levite, M., Neurotransmitters Activate T-Cells and Elicit Crucial Functions Via Neurotransmitter Receptor, *Curr Opin Pharmacol*, Aug. 2008, 8(4), 460-471.

Li, J., et al., Anti-Tgf-β Treatment Promotes Rapid Healing of Leishmania Major Infection in Mice by Enhancing In Vivo Nitric Oxide Production, *J Immunol*, 1999, 162, 974-979.

Lipton, S.A., et al., Dementia Associated With the Acquired Immunodeficiency Syndrome, *N Engl J Med.*, Apr. 6, 1995, 332(14), 934-940.

Lissoni, P., et al., Increase in CD4 Cell Number in AIDS Patients With CD4 Count Below 200/mm3 by Neuroimmunotherapy With Subcutaneous Low-Dose IL-2 and the Pineal Hormone Melatonin, *Proc Annu Meet Am Soc Clin Oncol*, 1996, 15, A857.

Llorente, L., et al., Clinical and Biologic Effects of Anti-Interleukin-10 Monoclonal Antibody Administration in Systemic Lupus Erythematosus, *Arthritis Rheum*, Aug. 2000, 43(8), 1790-1800.

Lucey, D.R., et al., Type 1 and Type2 Cytokine Dysregulation in Human Infectious, Neoplastic, and Inflammatory Diseases, *Clin Microbiol Rev.*, Oct. 1996, 9(4), 532.562.

McEwen, B.S., Protective and Damaging Effects of Stress Mediators, *N Engl J Med.*, Jan. 15, 1998, 338(3), 171-179.

Mattson, M.P., BDNF and 5-HT: A Dynamic Duo in Age-related Neuronal Plasticity and Neurodegenerative Disorders, *Trends in Neurosciences*, Oct. 2004, 27(10), 589-594.

Matzinger, P., The Danger Model: A Renewed Sense of Self, *Science*, Apr. 12, 2002, 296(5566), 301-305.

Mengozzi M., et al., Chlorpromazine Specifically Inhibits Peripheral and Brain TNF Production, and Up-Regulates IL-10 Production, in Mice, *Immunology*, Jun. 1994, 82(2), 207-210.

Meredith, E.J., et al., Close Encounter of the Monoamine Kind: Immune Cells Betray Their Nervous Disposition, *Immunology*, Jul. 2005, 115(3), 289-295.

Mirovsky, Y., et al., Novel Synergistic Treatment of Ethanol Withdrawal Seizures in Rats With Dopamine and Serotonin Agonists, *Alcohol Clin Exp Res.*, Feb. 1995, 19(1), 160-163.

Moffett, J.R., et al., Tryptophan and the Immune Response, *Immunol Cell Biol*, Aug. 2003, 81(4), 247-265.

Mogilnicka, E., et al., The Influence of Antiserotonergic Agents on the Action of Dopaminergic Drugs, *Pol J Pharmacol Pharm*, Jan.-Feb. 1977, 29(1), 31-38.

Mosmann, T.R., Cytokine Patterns During the Progression to AIDS, *Science*, Jul. 8, 1994, 265(5169), 193-194.

Moss, R.B., et al., Th1/Th2 Cells in Inflammatory Disease States: Therapeutic Implications, *Expert Opin Biol Ther.*, Dec. 2004, 4(12), 1887-1896.

Muller, T., et al., 5-Hydroxytryptamine Modulates Migration, Cytokine, and Chemokine Release and T-Cell Priming Capacity of Dendritic Cells In Vitro and In Vivo, *PLoS ONE*, Jul. 2009, 4(7), e6453-e6460. [online] [retrieved Apr. 29, 2010] URL: http://www.ncbi.nlm.nih.gov/pmc/articles/PMC2714071/pdf/pone.0006453.pdf.

Naldini, A., et al., Regulation of Angiogenesis by Th1- and Th2-Type Cytokines, *Current Pharmaceutical Design*, 2003, 9(7), 511-519.

Nestler, E.J., Is There a Common Molecular Pathway for Addiction?, *Nature Neuroscience*, Nov. 2005, 8(11), 1445-1449.

Nestler, E.J., The Neurobiology of Cocaine Addiction, *Science & Practice Perspectives*, Dec. 2005, 4-12.

Nic Dhonnchadha, B.A., et al., Serotonergic Mehcanisms in Addition-Related Memories, *Behav Brain Res*, Dec. 16, 2008, 195(1):39-53.

Nilsson, J., Regulating Protective Immunity in Atherosclerosis, *Circ. Res.*, 2005, 96, 395-397.

Nussenblatt, R.B., et al., Treatment of Noninfectious Intermediate and Posterior Uveitis With the Humanized Anti-Tac mAb: A Phase I/II Clinical Trial, *Proc Natl Acad Sci*, Jun. 1999, 96, 7462-7466.

Oades, R.D., Dopamine-Serotonin Interactions in Attention-deficit Hyperactivity Disorder (ADHD), *Prog Brain Res*, 2008, 172, 543-65.

Okura, Y., Recombinant Murine Interleukin-12 Facillitates Induction of Cardiac Myosin-Specific Type 1 Helper T Cells in Rats, *Circ Res*, Jun. 1, 1998, 82(10), 1035-1042.

Partridge, L., et al., Beyond the Evolutionary Theory of Ageing, from Functional Genomics to Evo-Gero, *Trends Ecol Evol.*, Jun. 2006, 21(6), 334-340.

Pene, J., et al., IgE Production by Normal Human Lymphocytes is Induced by Interleukin 4 and Suppressed by Interferons γ and α and Prostaglandin $E_2$, *Proc Natl Acad Sci*, Sep. 1988, 85, 6880-6884.

Pierucci, M., et al., Stimulation of Serotonin$_{2C}$ Receptors Blocks the Hyperactivation of Midbrain Dopamine Neurons Induced by Nicotine Administration, *J Pharmacol Exper Ther*, Apr. 2004, 309(1), 109-118.

Podwinska, J., et al., The Pattern and Level of Cytokines Secreted by Th1 and Th2 Lymphocytes of Syphilitic Patients Correlate to the Progression of the Disease, *FEMS Immunol Med Microbiol*, May 2000, 28(1), 1-14.

Presgraves, S.P., et al., Involvement of Dopamine $D_2/F_3$ Receptors and BDNF in the Neuroprotective Effects of S32504 and Pramipexole Against 1-Methyl-4-Phenylpyridinium in Terminally Differentiated SH-SY5Y Cells, *Exp Neurol.*, Nov. 2004, 190(1), 157-170.

Reuben, J.M., et al., Restoration of Th1 Cytokine Synthesis by T Cells of Patients With Chronic Myelogenous Leukemia in Cytogenetice and Hematologic Remission With Interferon-a, *Clin Cancer Res*, May 2000, 6(5), 1671-1677.

Robertson, A-K. L., et al., T Cells in Atherogenesis: For Better or For Worse?, *Anterioscler Throm Vasc Biol*, 2006, 26, 2421-2432.

Romagnani, S., et al., CD30 and Type 2 T Helper (Th2) Responses, *J Leukoc Biol*, May 1995, 57(5), 726-730.

Roper, S.D., Parallel Processing in Mammalian Taste Buds?, *Physiol Behav.*, Jul. 14, 2009, 97(5), 604-608.

Rothman, R.B., et al., Dual Dopamine/Serotonin Releasers: Potential Treatment Agents for Stimulant Addiction, *Exp Clin Psychopharmacol*, Dec. 2008, 16(6): 458-74.

Rothman, R.B., et al., Dual Dopamine/Serotonin Releasers as Potential Medications for Stimulante and Alcohol Addictions, *The AAPS Journal*, 2007, 9 (1), E1-E10, [online] [retrieved on May 25, 2010] URL: http://www.aapsj.org/articles/aapsj0901/appsj0901001/aapsj0901001.pdf.

Rothman, R.B., et al., Balance Between Dopamine and Serotonin Release Modulates Behavioral Effects of Amphetamine-Type Drugs, *Annals New York Academy of Science*, 2006, 1074, 245-260.

Rothman, R.B., et al. Phentermine and Fenfluramine: Preclinical Studies in Animal Models of Cocaine Addiction, *Ann N Y Acad Sci*, May 30, 1998, 844, 59-74.

Rothman, R.B., et al., Hypothesis that Mesolimbic Dopamine (DA) Plays a Key Role in Mediating the Reinforcing Effects of Drugs of Abuse as Well as the Rewarding Effects of Ingestive Behaviors, *J Subst Abuse Treat.*, May-Jun. 1994, 11(3), 273-275.

Sahelian. R., Serotonin Supplements that Work [online] [retrieved on Apr. 26, 2010] URL: http://www.raysahelian.com/serotonin.html.

Samoilova, E.B., et al., CD4OL Blockade Prevents Autoimmune Encephalomyelitis and Hampers TH1 but not TH2 Pathway of T Cell Differentiation, *J Mol Med*, Aug. 1997, 75(8), 603-608.

Sanni, L.A., et al., Dramatic Changes in Oxidative Tryptophan Metabolism Along the Kynurenine Pathway in Experimental Cerebral and Noncerebral Malaria, *Am J Pathol*, Feb. 1998, 152(2), 611-619.

Schandene, L., et al., Interferon Alpha Prevents Spontaneous Apoptosis of Clonal Th2 Cells Associated With Chronic Hypereosinophilia, *Blood*, Dec. 15, 2000, 96(13), 4285-4292.

Selye, H., A Syndrome Produced by Diverse Nocuous Agents, *J Neuropsychiatry Clin Neurosic*, May 1998, 10, 230-231.

Serafeim, A., et al., The Immune System Gets Nervous, *Curr Opin Pharmacol*, Aug. 2001, 1(4), 398-403.

Serafeim, A., et al., 5-Hydroxytryptamine Drives Apoptosis in Biopsylike Burkitt Lymphoma Cells: Reversal by Selective Serotonin Reuptake Inhibitors, *Blood*, Apr. 1, 2002, 99(7), 2545-2553.

Serafeim, A., et al., Selective Serotonin Reuptake Inhibitors Directly Signal for Apoptosis in Biopsy-Like Burkitt Lymphoma Cells, *Blood*, Apr. 15, 2003, 101(8), 3212-3219.

Serreze, D.V., et al., Th1 to Th2 Cytokine Shifts in Nonobese Diabetic Mice: Sometimes an Outcome, Rather than the Cause, of Diabetes Resistance Elicited by Immunostimulation, *J. Immunol*, Jan. 15, 2001, 166(2), 1352-1359.

Shimada, K., et al., Early Intervention Imbalance With Atorvastatin Modulates TH1/TH2 Imbalance in Patients With Acute Coronary Syndrome: From Bedside to Bench, *Circulation*, May 11, 2004, 104(18), e213-e214.

Shirota, H., et al., Regulation of Murine Airway Eosinophilia and Th Cells by Antigen-Conjugated CpG Oligodeoxynucleotides as a Novel Antigen-Specific Immunomodulator, *J Immunol*, 2000, 164, 5575-5582.

Silva De Lima, M, et al., Pharmacological Treatment of Cocaine Dependence: A Systematic Review, *Addiction*, Aug. 2002, 97(8), 931-949.

Slassi, A., et al., Recent Progress in 5-$HT_7$ Receptors: Potential Treatment of Central and Peripheral Nervous System Diseases, *Expert Opin. Ther. Patents*, 2004, 14(7), 1009-1027.

Stohlman, S.A., et al., Activation of Regulatory Cells Suppresses Experimental Allergic Encephalomyelitis Via Secretion of IL-10, *J Immunol*, Dec. 1, 1999, 163(11), 6338-6344.

Takikawa, O., et al., Mechanism of Interferon-γ Action.Characterization of Indoleamine 2,3-Dioxygenase in Cultured Human Cells Induced by Interferon-γ and Elevation of the Enzyme-Mediated Tryptophan Degradation in its Anticellular Activity, *The Journal of Biological Chemistry*, Feb. 5, 1988, 263, 2041-2048.

Targan, S.R., et al., A Short-Term Study of Chimeric Monoclonal Antibody cA2 to Tumor Necrosis Factor Alpha for Crohn's Disease. Crohn's Disease cA2 Study Group, *N Engl J Med*, Oct. 9, 1997, 337(15), 1029-1035.

Trabattoni, D., et al., Augmented Type 1 Cytokines and Human Endogenous Retrovirus Specific Immune Responses in Patients With Acute Multiple Sclerosis, *J Neurovirol*, May 2000, 6(Suppl 2), S38-S41.

Tracey, K.J., The Inflammatory Reflex, *Nature*, Dec. 19, 2002, 420, 853-859.

Weintraub, D., Dopamine and Impulse Control Disorders in Parkinson's Disease, *Annals of Neurology*, Aug. 2008, 64(S2): S93-S100.

Whooley, M.A., et al., Managing Depression in Medical Outpatients, *N Engl J Med*, Dec. 28, 2000, 343(26), 1942-1950 [online] [retrieved Apr. 28, 2010] URL: file:///C:/DOCUME~1/owner/LOCALS~1/Temp/2152%20Whooley-1.htm.

Wittig, B., et al., Curative Treatment of an Experimentally Induced Colitis by a CD44 Variant V7-Specific Antibody, *J Immunol*, Aug. 1, 1998, 161(3), 1069-1073.

Wynn, T.A., Fibrotic Disease and the $T_H1/T_H2$ Paradigm, *Nat Rev Immunol*, Aug. 2004, 4(8), 583-594.

Xiao, Y.L., et al., Neuroprotective Mechanism of Modafinil on Parkinson Disease Induced by 1-Methyl-4-Phenyl-1,2,3,6-Tetrahydropyridine, *Acta Pharmacol Sin*, Mar. 2004, 25(3), 301-305.

Yasui, H., et al., Interferon Enhances Tryptophan Metabolism by Inducing Pulmonary Indoleamine 2,3-Dioxygenase: Its Possible Occurence in Cancer Patients, *Proc Natl Acad Sci USA*, Sep. 1986, 83(17), 6622-6626.

Youssef, S., et al., The HMG-CoA Reductase Inhibitor, Atorvastatin, Promotes a Th2 Bias and Reverses Paralysis in Central Nervous System Autoimmune Disease, *Nature*, Nov. 7, 2002, 420(6911), 78-84.

Zhou, X, et al., Hypercholesterolemia is Associated With a T Helper (Th) 1/Th2 Switch of the Autoimmune Response in Atherosclerotic Apo E-Knockout Mice, *J. Clin. Invest.*, Apr. 1998, 101(8), 1717-1725.

Dopamine Boost Affects Cocaine Use in Rats [online], Apr. 17, 2008 [retrieved on Jan. 28, 2009] URL:http://www.jointogether.org/news/researchlsummaries/2008/dopamine-boost-affects-cocaine.html.

CHK Nutrition Neurotransmitter Chemistry [online] [retrieved on Apr. 26, 2010] URL: http://www.chknutrition.com/Neurotransmitter_Chemistry.htm.

Serotonin Kills Pain—And May Be Available From Your Subconscious [online] [retrieved on Apr. 28, 2010] URL: http://iridolooynow.sandycarter.com/alternative/6086.php.

* cited by examiner

TASTE TITRATION THERAPIES

CROSS-REFERENCE TO RELATED APPLICATIONS

This application claims the benefit of U.S. Provisional Application No. 61/011,369, filed Jan. 17, 2008, which is hereby incorporated herein by reference in its entirety.

BACKGROUND

1. Field of the Invention

The teachings provided herein relate to the preparation and uses of formulations comprising a serotonergic agent or a dopaminergic agent for oral transmucosal delivery using a taste titration.

2. Description of Related Art

The monoamines dopamine and serotonin are major central nervous system neurotransmitters. Their deficiencies in the CNS or imbalance are associated with multiple disorders. Multiple medications have been used therapeutically to increase the levels of dopamine and serotonin in the central nervous system.

In 1971, President Nixon declared a "war on drugs." It has not gone well. For the last decade, the direct and indirect costs to society of drug and alcohol abuse in the United States alone has approached $4 trillion. In the United States, since 1998, there have been more than 30,000 drug-related homicides, as well as 250,000 alcohol-related vehicular deaths, and that is just the beginning. One cannot forget the anonymous personal tragedies that never hit the charts. The abuse of illicit drugs such as psychostimulants, for example, is a problem worldwide, and few treatments are available for treating such drug abuse and addiction. Monoamine releasers have been used as agonists to attempt treatment of cocaine addiction and alleviate withdrawal symptoms, as well as relapse. Unfortunately, some of the treatments also possess the potential for abuse due to the activation of mesolimbic dopamine neurons in reward pathways. It's been suggested that serotonin administration may be administered to offset this problem, such that achieving a dopamine/serotonin balance could be a successful treatment regime for such addictions. Rothman, et al., have studied various agonist therapies on rats and monkeys, with limited success, in which the research directed to discovering single molecule agonists that are dual releasers of both dopamine and serotonin. See Rothman, et al. Ann. N.Y. Acad. Sci. 1074:245-260 (2006); see also Rothman, et al. Exp Clin Psychopharmacol. 16(6):458-74 (2008).

Treatments directed to addressing serotonin and dopamine deficits have also been used for affective disorders, attention deficit disorder, attention deficit hyperactivity disorder, and autism. Unfortunately, there have been a number of problems associated with currently available treatments, such as not knowing the levels of agent that need to be administered for a particular patient, overdosing administration of agents, achieving a neurotransmitter imbalance, and long wait-times to determine effectiveness of a given treatment. Doctors have had to monitor patients very closely to make adjustments and estimate the proper balance between the neurotransmitters. And, it doesn't help that many activities of daily life also affect the neurotransmitter balance and add to the guesswork, such as food intake, stress, exercise, drugs taken, and the like. For example, when administering selective serotonin reuptake inhibitors (SSRIs), doctors tell patients that it will take a month before they know if the treatment is effective. In addition, overdoses that occur through such treatments have been suggested as the cause of suicides, since the overdoses can exacerbate some disorders. Sometimes other drugs must be added to current treatment methods to treat side effects, and sometimes these additional drugs have their own side effects.

One of skill will appreciate formulations, systems, and methods of administering serotonergic agents and dopaminergic agents that have the ability to remit deficiencies and imbalances in a subject's serotonin and dopamine levels. One of skill will particularly appreciate formulations, systems, and methods of administering serotonergic agents and dopaminergic agents that reduce or remove the guesswork associated with current therapies, as well as the side effects that may also be experienced. The formulations, systems, and methods taught herein provide several advantages over the state-of-the art, such that they at least enable (1) the patient and doctor to readily determine the correct dosages, (2) a quick measure of effectiveness of a treatment, (3) a use of a chemical pathway that is desirable, (4) a quick delivery of the agents across the blood-brain barrier through the use of oral transmucosal delivery, minimizing the amount of free metabolites circulating in the body, (5) an inherent adjustment in the amounts of agents administered to compensate for changes in the level of imbalance in neurotransmitter levels, (6) a non-frightening and pleasant treatment for many disorders suffered by a patient, (7) a mitigated risk of overdose to a patient through the simple taste response, and (8) an easy identification of the correct neurotransmitter balance in the subject by the doctor and the patient.

SUMMARY

The teachings provided herein generally relate to the preparation and uses of a formulation comprising a serotonergic agent or dopaminergic agent in a form capable of oral transmucosal delivery to a subject. The formulation includes a flavoring agent and a carrier base. The flavoring agent functions as a taste indicator of the endpoint of a taste titration of the serotonergic or dopaminergic agent for a subject receiving an oral administration of the formulation in the form of a taste titration, and the endpoint is indicated to the subject by a change in the intensity of the flavor of the flavoring agent.

The serotonergic agent or dopaminergic agent can comprise a hydroxylated aromatic acid monoamine precursor to serotonin or dopamine. In some embodiments, the serotonergic agent comprises 5-hydroxytryptophan, such as the L-isomer, the D-isomer, or a racemic mixture of the 5-hydroxytryptophan. And, in some embodiments, the dopaminergic agent comprises levodopa.

5-hydroxytryptophan and levodopa are precursors of serotonin and dopamine. When 5-hydroxytryptophan and levodopa are swallowed, they are decarboxylated by an enzyme in the liver and become serotonin and dopamine, neither of which can pass the blood-brain barrier. This is known as a first-pass effect. However, if the 5-hydroxytryptophan and levodopa are administered oral transmucosally, the first-pass effect is avoided, and delivery of the 5-hydroxytryptophan and levodopa to the central nervous system is realized, where they are quickly metabolized into serotonin and dopamine.

The flavoring agent can have a pleasant flavor and, in some embodiments, the flavoring agent comprises a sweetening agent. The formulation can further comprise a flavor-endpoint agent that has a flavor that (i) is at least substantially unnoticed by the subject at the start of the titration and (ii) becomes at least substantially noticed by the subject at the end of the titration. The flavor-endpoint agent can have an unpleasant flavor and, in some embodiments, the flavor-endpoint agent can have a bitter flavor.

The formulations described above can be administered as a system. As such, the teachings are also directed to a system for use in balancing neurotransmitter levels in a subject through a taste titration. The system includes a serotonergic formulation comprising a serotonergic agent, a first flavoring agent, and a first carrier base. The first flavoring agent functions as a taste indicator of the endpoint of a taste titration of the serotonergic agent for the subject receiving the serotonergic formulation. The endpoint is indicated to the subject by a change in the intensity of the flavor of the first flavoring agent. The system also includes a dopaminergic formulation comprising a dopaminergic agent, a second flavoring agent, and a second carrier base. The second flavoring agent functions as a taste indicator of the endpoint of the taste titration of the dopaminergic agent for the subject receiving the dopaminergic formulation. The endpoint is indicated to the subject by a change in the intensity of the flavor of the second flavoring agent. The serotonergic formulation and the dopaminergic formulation function together to remit deficiencies and imbalances in the subject's serotonin and dopamine levels.

In some embodiments, the serotonergic formulation or the dopaminergic formulation is in the form of a liquid for administering to the subject's tongue or oral mucosa. In some embodiments, the serotonergic formulation or the dopaminergic formulation is in the form of a solid for administering to the subject's tongue or oral mucosa. In some embodiments, the serotonergic formulation or the dopaminergic formulation is in the form of a lozenge for administering to the subject's tongue or oral mucosa, such that the lozenge functions to perform the titration through an oral dissolution of the lozenge in the subject.

In some embodiments, the serotonergic agent can contain a first coloring agent and the dopaminergic agent can contain a second coloring agent, wherein the color of the first coloring agent and the color of the second coloring are distinguishable to the subject.

The teachings are also directed to a method of using the formulations and system described above for balancing neurotransmitter levels in a subject through a taste titration. The method comprises orally administering a serotonergic formulation comprising a serotonergic agent, a first flavoring agent, and a first carrier base to a first endpoint of a taste titration of the serotonergic formulation. The first flavoring agent functions as a taste indicator of the first endpoint for the subject receiving the serotonergic formulation, and the first endpoint is identified by a change in the intensity of the flavor of the first flavoring agent to the subject. The serotonergic agent is delivered to the subject oral transmucosally. The next step includes ceasing the administering of the serotonergic formulation at the first endpoint. The method also includes orally administering a dopaminergic formulation comprising a dopaminergic agent, a second flavoring agent, and a second carrier base to a second endpoint of a taste titration of the dopaminergic formulation. The second flavoring agent functions as a taste indicator of the second endpoint for the subject receiving the dopaminergic formulation, wherein the second endpoint is identified by a change in the intensity of the flavor of the second flavoring agent to the subject. The dopaminergic agent is delivered to the subject oral transmucosally. The next step includes ceasing the administering of the dopaminergic agent formulation at the second endpoint. The serotonergic formulation and the dopaminergic formulation function together to remit deficiencies and imbalances in the subject's serotonin and dopamine levels.

The teachings are also directed to a method of using one of the formulations for remitting a deficiency in a neurotransmitter level in a subject through a taste titration. The method comprises orally administering a serotonergic agent or a dopaminergic agent in a formulation. The serotonergic agent or the dopaminergic agent can be delivered to the subject oral transmucosally. The formulation further comprises a flavoring agent and a carrier base. The flavoring agent can function as a taste indicator of the endpoint of a taste titration of the serotonergic or dopaminergic agent for a subject receiving an oral administration of the formulation, and the endpoint is indicated to the subject by a change in the intensity of the flavor of the flavoring agent. The next step includes ceasing the administering of the formulation at the endpoint. The serotonergic formulation and the dopaminergic formulation function together to remit deficiencies and imbalances in the subject's serotonin and dopamine levels.

The formulations, systems, and methods can be used to treat disorders. Any disorder, or symptom of a disorder, that is known to one of skill to be associated with dopamine and serotonin levels may be treatable using the teachings provided herein. In some embodiments, the method can be used to ameliorate cravings or ameliorate withdrawal symptoms in the treatment of an addictive disorder. In some embodiments, the method can be used to treat an affective disorder, an obsessive or compulsive disorder, an immune disorder, an autoimmune disorder, or a neurodegenerative disorder. In some embodiments, the neurodegenerative disorder can include, for example, amyotrophic lateral sclerosis or fibromyalgia.

One of skill reading the teachings that follow will appreciate that the concepts can extend into additional embodiments that go well-beyond a literal reading of the claims, the inventions recited by the claims, and the terms recited in the claims.

DETAILED DESCRIPTION

The teachings provided herein generally relate to the preparation and uses of a formulation comprising a serotonergic agent or dopaminergic agent in a form capable of oral transmucosal delivery to a subject. The formulation includes a flavoring agent and a carrier base. The flavoring agent functions as a taste indicator of the endpoint of a taste titration of the serotonergic or dopaminergic agent for a subject receiving an oral administration of the formulation in the form of a taste titration, and the endpoint is indicated to the subject by a change in the intensity of the flavor of the flavoring agent. The taste titration is based on a change in flavor, so the taste titration is also referred to as a "flavorimetric titration."

In some embodiments, a change in the intensity of flavor is sufficient as a titration endpoint when the taste transforms from pleasant to bland, from intensely pleasant to mildly pleasant, from pleasant to non-existent, or from pleasant to unpleasant. In some embodiments, a change in the intensity of flavor is sufficient as a titration endpoint when the taste transforms from unpleasant to bland, from intensely unpleasant to mildly unpleasant, from unpleasant to non-existent, or from unpleasant to pleasant.

Without intending to be bound by any theory or mechanism of action, it is believed that, as a neurotransmitter's deficit is remitted using the methods taught herein, the brain sends a message to the subject's tongue to decrease the pleasant taste of a flavored formulation and, the administration is stopped at the taste endpoint. If the administration continues, the brain sends a signal of nausea in a further attempt to stop the subject from administering more of the formulation. The principle suggested is that neurotransmitters affect taste to regulate intake of substances that affect dopamine and serotonin levels. In some embodiments, a deficiency in a neurotransmitter is remitted when, for example, there is a measurable response in a subject that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of a desired response.

The formulations, systems, and methods can be used to treat disorders. Any disorder, or symptom of a disorder, that is known to one of skill to be associated with dopamine and serotonin levels may be treatable using the teachings provided herein. In some embodiments, the method can be used to ameliorate cravings or ameliorate withdrawal symptoms in the treatment of an addictive disorder. In some embodiments, the method can be used to treat an affective disorder, an obsessive or compulsive disorder, an immune disorder, an autoimmune disorder, or a neurodegenerative disorder. Examples of some disorders, such as immune disorders, that are contemplated to be treatable by the teachings provided herein include, for example, those conditions taught in U.S. Pat. No. 5,502,080, which is hereby incorporated by reference in its entirety. The terms "treat," "treatment", and "treating" include, for example, the therapeutic and/or prophylactic uses in the prevention of a disease, inhibition of a disease, and/or amelioration of symptoms of disease. The term "subject" and "patient" can be used interchangeably and refer to an animal such as a mammal including, but not limited to, non-primates such as, for example, a cow, pig, horse, cat, dog, rat and mouse; and primates such as, for example, a monkey or a human.

In some embodiments, the formulations, systems, and methods can be used to treat drug and alcohol craving; drug and alcohol withdrawal symptoms; immediate hypersensitivity disorders, such as asthma, anaphylaxis, allergic and non-allergic rhinitis; the symptoms associated with immediate hypersensitivity disorders, such as wheezing, dyspnea, rhinitis, urticaria, and pruritus; autoimmune disorders; immunodeficiency disorders such as, for example, HIV; neurodegenerative disorders such as, for example, multiple sclerosis, Alzheimer's Disease, Parkinson's Disease, and amyotrophic lateral sclerosis; dysphorias associated with affective disorders, including depression, anxiety, and hostility; obsessive/compulsive ideations and behaviors; ideations associated with eating disorders; fibromyalgia; Gulf War Syndrome, post-traumatic stress disorder; chronic fatigue immune deficiency disorder; attention deficit disorder and attention deficit hyperactivity disorder; and the like. In some embodiments, the formulations, systems, and methods are contemplated for use in treating any disorder that includes an imbalance of the ratio of type-1 T-helper cells to type-2 T-helper cells.

A "titration" can include any oral administration, or combination of oral administrations, that facilitates a gradual oral transmucosal delivery of the serotonergic agent or dopaminergic agent to a subject. The formulations can be in any oral dosage form known to one of skill that could provide a suitable and reproducible titration of the serotonergic agent or dopaminergic agent. Generally speaking, however, one of skill will appreciate that oral dosage forms comprise liquids (solutions, suspensions, and emulsions), and solids (powders, granules, and lozenges).

In some embodiments, the formulation can be in the form of a solution. The titration includes orally administering the serotonergic formulation or the dopaminergic formulation in the form of a solution to the subject's tongue or oral mucosa and ceasing administration at the endpoint, such that the solution functions to perform the titration through delivery of the agent in the solution in the subject. A solution is a mixture of components that form a single phase that is homogeneous down to the molecular level. Solutions offer several advantages over other dosage forms. Compared with solid dosage forms, solutions are absorbed faster and generally cause less irritation of the GI mucosa. Moreover, phase separation on storage is not a concern with solutions, as it may be for suspensions and emulsions. The disadvantages of solutions include susceptibility to microbial contamination and the hydrolysis in aqueous solution of susceptible active ingredients. A range of additives can be used in the formulation of oral solutions, including buffers, flavors, antioxidants, and preservatives.

In some embodiments, the formulation can be in the form of a suspension. The titration includes orally administering the serotonergic formulation or the dopaminergic formulation in the form of a suspension to the subject's tongue or oral mucosa and ceasing administration at the endpoint, such that the suspension functions to perform the titration through delivery of the agent in the suspension in the subject. A suspension is a coarse dispersion of insoluble drug particles, generally with a diameter exceeding 1 μm, in a liquid (usually aqueous) medium. Taste may be less noticeable in suspension than in solution. Particle size is an important determinant of the dissolution rate and bioavailability of the agents in suspension. In addition to the excipients described above for solutions, suspensions include surfactants and thickening agents. Surfactants wet the solid particles, thereby ensuring the particles disperse readily throughout the liquid. Thickening agents reduce the rate at which particles settle to the bottom of the container. Some settling is acceptable, provided the sediment can be readily dispersed when the container is shaken.

In some embodiments, the formulation can be in the form of an emulsion. The titration includes orally administering the serotonergic formulation or the dopaminergic formulation in the form of an emulsion to the subject's tongue or oral mucosa and ceasing administration at the endpoint, such that the emulsion function to perform the titration through delivery of the agent in the emulsion in the subject. An emulsion is a system consisting of 2 immiscible liquid phases, one of which is dispersed throughout the other in the form of fine droplets; droplet diameter generally ranges from 0.1-100 μm. Emulsions are stabilized through the use of an emulsifying agent, which prevents coalescence of the dispersed droplets. Creaming is undesirable, but it is not a serious problem because a uniform dispersion returns upon shaking. Other additives include buffers, antioxidants, and preservatives. Emulsions for oral administration are usually oil (the active ingredient) in water.

In some embodiments, the formulation can be in the form of a powder. The titration includes orally administering the serotonergic formulation or the dopaminergic formulation in the form of a powder to the subject's tongue or oral mucosa and ceasing administration at the endpoint, such that the powder functions to perform the titration through an oral dissolution of the powder in the subject. A powder is a formulation in which a drug powder is mixed with other powdered excipients to produce a final product for oral administration. Powders have better chemical stability than liquids. Tastes can be more pronounced with powders than with other dosage forms.

In some embodiments, the formulation can be in the form of a granule. The titration includes orally administering the serotonergic formulation or the dopaminergic formulation in the form of a granule to the subject's tongue or oral mucosa and ceasing administration at the endpoint, such that the granule functions to perform the titration through an oral dissolution of the granule in the subject. A granule is a dosage form consisting of powder particles that have been aggregated to form a larger mass, usually 2-4 mm in diameter. Granulation overcomes segregation of the different particle sizes during storage and/or dose administration, the latter being a potential source of inaccurate dosing. Granules and powders generally behave similarly; however, granules must deaggregate prior to dissolution and absorption.

In some embodiments, the formulation can be in the form of a lozenge or troche. The titration includes orally administering the serotonergic formulation or the dopaminergic formulation in the form of a lozenge to the subject's tongue or oral mucosa and ceasing administration at the endpoint, such that the lozenge function to perform the titration through an oral dissolution of the lozenge in the subject. The lozenge can be any solid form, such as an individually wrapped "hard candy-like" substance and, in some embodiments, the lozenge can be on a stick, such as a candy-like "sucker" substance. In some embodiments, the lozenge can be removed for later use at the endpoint of the titration and, in some embodiments, the lozenge can be swallowed at the endpoint of the titration.

In some embodiments, the formulation can be administered as a spray. The titration includes orally administering the serotonergic formulation or the dopaminergic formulation in the form of a spray to the subject's tongue or oral mucosa and ceasing administration at the endpoint. The spray can be a pump or aerosol spray, in some embodiments.

Serotonergic agents can include, for example, substances that affect the neurotransmitter serotonin or the components of the nervous system that use serotonin. Such agents, can include, for example, serotonin precursors, such as tryptophan and 5-hydroxytryptphan (5-HTP); cofactors required in the body's production of serotonin, such as Vitamin C; serotonin agonists; serotonergic enzymes; selective serotonin reuptake inhibitors (SSRIs), such as PAXIL, PROZAC, and ZOLOFT; noradrenergic and specific serotonergic antidepressants, such as serotonin norepinephrine reuptake inhibitors (SNRI), tricyclic antidepressants, and monoamine oxidase inhibitors (MAOIs); and serotonergic psychedelics, such as LSD, psilocybin, DMT and mescaline. Examples of serotonin agonists can be found, for example, in U.S. Pat. No. 5,502,080, which is hereby incorporated by reference in its entirety.

Dopaminergic agents can include, for example, substances that affect the neurotransmitter dopamine or the components of the nervous system that use dopamine, such as dopamine precursors, including levodopa, phenylalanine, tyrosine; cofactors required in the body's production of dopamine, such as Vitamin C, Vitamin B6; dopamine agonists, such as pergolide; MAOIs, such as selegililne; and dopamine reuptake inhibitors, such as buproprion. Examples of dopamine agonists can be found, for example, in U.S. Pat. No. 5,502,080, which is hereby incorporated by reference in its entirety.

Some agents can be serotonergic or dopaminergic, which is distinguishable from agents that affect only serotonin levels or only dopamine. One of skill will recognize, for example, that theanine increases serotonin and dopamine, whereas yohimbine and tolcapone increases dopamine.

The serotonergic agent or dopaminergic agent can comprise a hydroxylated aromatic acid monoamine precursor to serotonin or dopamine. In some embodiments, the serotonergic agent comprises 5-hydroxytryptophan. And, in some embodiments, the dopaminergic agent comprises levodopa. In some embodiments, the concentration of the 5-hydroxytryptophan or levodopa in the formulation can range from about 5 mg/ml to about 750 mg/ml, from about 60 mg/ml to about 180 mg/ml, from about 15 mg/ml to about 500 mg/ml, from about 25 mg/ml to about 250 mg/ml, from about 50 mg/ml to about 150 mg/ml, from about 30 mg/ml to about 100 mg/ml, or any range therein.

The flavoring agent can have a pleasant flavor and, in some embodiments, the flavoring agent comprises a sweetening agent. The formulation can further comprise a flavor-endpoint agent that has a flavor that (i) is at least substantially unnoticed by the subject at the start of the titration and (ii) becomes at least substantially noticed by the subject at the end of the titration. The flavor-endpoint agent can have an unpleasant flavor and, in some embodiments, the flavor-endpoint agent can have a bitter flavor. In some embodiments, the flavor-endpoint agent can accompany a formulation comprising 5-hydroxytryptophan. And, in some embodiments, the flavor-endpoint agent can accompany a formulation comprising levodopa.

The flavoring agent can function to provide any flavor desired for use in the taste titration. In some embodiments, the flavor can be pleasant to the subject, such as flavor that sweet or tart, and the endpoint of the titration can be marked by a decrease in the pleasant flavor. In some embodiments, the flavor can be unpleasant to the subject, such as flavor that is bitter or sour, and the endpoint of the titration can be marked by a decrease in the unpleasant flavor. In some embodiments, the flavoring agent comprises a sweetening agent. Examples of sweetening agents can include, but are not limited to, stevia, sucrose, aspartame, ORABASE, saccharin, acesulfame potassium, xylitol, alitame, dextrose, fructose, glucose, glycerine, lacitol, maltitol, maltose, mannitol, polydextrose, sodium cyclamate, sorbitol, and trehalose.

One of skill will appreciate that the carrier base can be any substance for carrying the components of the formulation to the subject during the titration for taste and assimilation of the components of the formulation. In some embodiments, the carrier base easily releases the active ingredients to the user for rapid taste and assimilation of the components of the formulation. Examples of carrier bases can include, but are not limited to, syrup, glycerine, water, gelatin, troche bases, olive, almond oil, glycerine, propylene glycol, and the like.

One of skill will appreciate that the flavor-endpoint agent can be any such agent having a flavor that would make the flavor-threshold of the taste titration more noticeable to the subject. The flavor of the flavor-endpoint agent can be initially masked by the flavoring agent and then stand out as the flavor of the flavoring agent dissipates during the taste titration. In some embodiments, the flavoring agent can have a pleasant flavor, such as a sweet or tart flavor, and the flavor-endpoint agent may have an unpleasant flavor, such as a bitter or sour flavor. For example, the flavoring agent can be a sweetening agent, where the flavor-endpoint agent would be initially masked by the sweet flavor but would stand out as an unpleasant bitter or sour flavor as the pleasant sweetness dissipates to the user during the course of the taste titration. In some embodiments, the flavoring agent can have an unpleasant flavor, such as a bitter or sour flavor, and the flavor-endpoint agent may have a pleasant flavor, such as a sweet or tart flavor. Examples of flavor-endpoint agents can include, but are not limited to, quinine, chocolate, citric acid, and the like. A flavor-endpoint agent is "substantially unnoticed," for example, where the pleasantness or unpleasantness of the flavor-endpoint agent is not the predominating taste experienced by the subject. A flavor-endpoint agent is "substantially noticed," for example, where the pleasantness or unpleasantness of the flavor-endpoint agent is the predominating tasted experienced by the subject.

One of skill will appreciate that the formulation can include other ingredients such as, for example, additional flavoring agents, suspending agents, preservatives, or coloring agents.

The formulations described above can be administered as a system. As such, the teachings are also directed to a system for use in balancing neurotransmitter levels in a subject through a taste titration. The system includes a serotonergic formulation comprising a serotonergic agent, a first flavoring agent, and a first carrier base. The first flavoring agent functions as a taste indicator of the endpoint of a taste titration of the serotonergic agent for the subject receiving the serotonergic formulation. The endpoint is indicated to the subject by a change in the intensity of the flavor of the first flavoring agent. The system also includes a dopaminergic formulation comprising a dopaminergic agent, a second flavoring agent, and a second carrier base. The second flavoring agent functions as a taste indicator of the endpoint of the taste titration of the dopaminergic agent for the subject receiving the dopaminergic formulation. The endpoint is indicated to the subject by a change in the intensity of the flavor of the second flavoring agent. The serotonergic formulation and the dopaminergic formulation function together to remit deficiencies and imbalances in the subject's serotonin and dopamine levels.

In some embodiments, the serotonergic formulation or the dopaminergic formulation is in the form of a liquid for administering to the subject's tongue or oral mucosa. In some embodiments, the serotonergic formulation or the dopaminergic formulation is in the form of a solid for administering to the subject's tongue or oral mucosa. In some embodiments, the serotonergic formulation or the dopaminergic formulation is in the form of a lozenge for administering to the subject's tongue or oral mucosa, such that the lozenge functions to perform the titration through an oral dissolution of the lozenge in the subject.

In some embodiments, the serotonergic agent can contain a first coloring agent and the dopaminergic agent can contain a second coloring agent, wherein the color of the first coloring agent and the color of the second coloring are distinguishable to the subject.

The teachings are also directed to a method of using the formulations and system described above for balancing neurotransmitter levels in a subject through a taste titration. The method comprises orally administering a serotonergic formulation comprising a serotonergic agent, a first flavoring agent, and a first carrier base to a first endpoint of a taste titration of the serotonergic formulation. The first flavoring agent functions as a taste indicator of the first endpoint for the subject receiving the serotonergic formulation, and the first endpoint is identified by a change in the intensity of the flavor of the first flavoring agent to the subject. The serotonergic agent is delivered to the subject oral transmucosally. The next step includes ceasing the administering of the serotonergic formulation at the first endpoint. The method also includes orally administering a dopaminergic formulation comprising a dopaminergic agent, a second flavoring agent, and a second carrier base to a second endpoint of a taste titration of the dopaminergic formulation. The second flavoring agent functions as a taste indicator of the second endpoint for the subject receiving the dopaminergic formulation, wherein the second endpoint is identified by a change in the intensity of the flavor of the second flavoring agent to the subject. The dopaminergic agent is delivered to the subject oral transmucosally. The next step includes ceasing the administering of the dopaminergic agent formulation at the second endpoint. The serotonergic formulation and the dopaminergic formulation function together to remit deficiencies and imbalances in the subject's serotonin and dopamine levels.

In some embodiments, the effectiveness of the method is apparent rather quickly to the subject. In some embodiments, the effectiveness of the method is almost immediate or immediate, such that the desired results are noticeable to the subject.

In some embodiments, the titration includes orally administering the serotonergic formulation or the dopaminergic formulation in the form of a liquid to the subject's tongue or oral mucosa and ceasing administration at the endpoint. And, in some embodiments, the titration includes orally administering the serotonergic formulation or the dopaminergic formulation in the form of a solid to the subject's tongue or oral mucosa and ceasing administration at the endpoint. The order of the titration of the seroternergic formulation and the dopaminergic formulation can be inconsequential, in some embodiments, meaning that the terms "first" and "second" do not indicate any order of administration. For example, the serotonergic formulation can be titrated to blandness first, and the dopaminergic formulation can be titrated to blandness next. In contrast, and likewise, the dopaminergic formulation can be titrated to blandness first, and the serotonergic formulation can be titrated to blandness next. The process can be repeated to ensure that the neurotransmitters are in balance, and the order of the titrations may again be inconsequential.

The formulations, systems, and methods can be used to treat disorders. Any disorder, or symptom of a disorder, that is known to one of skill to be associated with dopamine and serotonin levels may be treatable using the teachings provided herein. In some embodiments, the method can be used to ameliorate cravings or ameliorate withdrawal symptoms in the treatment of an addictive disorder. In some embodiments, the method can be used to treat an affective disorder, an obsessive or compulsive disorder, an immune disorder, an autoimmune disorder, or a neurodegenerative disorder. In some embodiments, the neurodegenerative disorder can include, for example, amyotrophic lateral sclerosis or fibromyalgia.

In some embodiments, the method can be used to ameliorate cravings in the treatment of an addictive disorder. The term "addiction," in some embodiments, describes an obsession, compulsion, craving, or excessive physical dependence or psychological dependence, such as: drug addiction, crime, alcoholism, compulsive overeating, eating disorders such as anorexia nervosa and bulimia, problem gambling, computer addiction, pornography, sex, etc. In some embodiments, an addiction comprises a state in which the body relies on a substance for normal functioning and develops physical dependence, such as in drug addiction, and drug addiction includes nicotine addiction through smoking. For example, when the drug or substance on which someone is dependent is suddenly removed, it will cause withdrawal, a characteristic set of signs and symptoms.

In some embodiments, addiction can be associated with increased drug tolerance. In some embodiments, addiction is not necessarily associated with substance abuse since this form of addiction can result from using medication as prescribed by a doctor. In some embodiments, the term addiction can include psychological dependence. For example, the term can be used in drug addiction and substance abuse problems, and also refers to behaviors that are not generally recognized by the medical community as problems of addiction, such as compulsive overeating. Impulse control disorders, for example, include compulsive gambling, buying, sexual behavior, and eating. In some embodiments, the term addiction can be applied to compulsions that are not substance-related, such as problem gambling and computer addiction. In many embodiments, for example, the term addiction can be used to describe a recurring compulsion by an individual to engage in some specific activity, despite harmful consequences to the individual's health, mental state or social life.

In some embodiments, the method can be used to ameliorate withdrawal symptoms in the treatment of an addictive disorder. Withdrawal symptoms include uncomfortable physical or mental changes that happen when the body is deprived of an activity, for example, the alcohol or drugs that it is accustomed to getting. Withdrawal symptoms can last a few days to a few weeks and may include nausea or vomiting, sweating, shakiness, and anxiety. In some embodiments, withdrawal symptoms occur if a person has regular, heavy use of a drug or alcohol. In some embodiments, withdrawal symptoms can be extremely uncomfortable without professional help. In some embodiments, the withdrawal symptoms may be so severe that treatment for withdrawal may require a medical professional to be present. Drug and alcohol rehabilitation, for example, have been often used to overcome withdrawal symptoms and recovery from drug addiction.

In some embodiments, withdrawal symptoms can be severe, as well as life-threatening. The severity of the withdrawal symptoms can be based on many variables. These variables can include the type of activity, such as the type of drug, quantity of regular use, to the length of time the activity was abused. Of course, the type of activity of concern plays an important part in determining the length and severity of withdrawal symptoms. For example, an individual who uses methadone over a period of several months to years and decides to discontinue use will experience a longer and more painful withdrawal than an individual who discontinues using heroin.

Withdrawal symptoms can include, but are not limited to, weight loss, paranoia, and preoccupation. In some embodiments, a loss of appetite occurs when someone is addicted to drugs due to the body's constant craving for the drug, where the appetite for the drug exceeds a normal appetite for food, resulting in weight loss. Paranoia is a common withdrawal symptom for an addict and results from the activity, such as a drug, disrupting the normal mental functions and creating an obsessive thought that someone is out to get the addict. Preoccupation occurs because the addicts become preoccupied and often desperate in searching and acquiring the activity, such as a drug. Many will go to any lengths to obtain the drug of choice, for example, and that includes stealing, lying, fraud, and even violent crimes. A drug addict will likely steal from anyone or ask for money with no intentions on paying anyone back. Therefore, relationships, employment, health and hygiene often suffer.

In some embodiments, the method can be used in the treatment of an affective disorder. Affective disorders include psychiatric diseases and conditions having aspects that include biological, behavioral, social, and psychological factors. Examples of affective disorders include, but are not limited to, major depressive disorder, bipolar disorders, and anxiety disorders. Affective disorders can result, for example, in symptoms ranging from the mild and inconvenient to the severe and life-threatening; the latter account for more than 15% of deaths due to suicide among those with one of the disorders. Hostility, on the other hand, can be considered an affective disorder in itself.

In some embodiments, the method can be used in the treatment of an obsessive or compulsive disorder. Disorders that comprise an obsession are those that include an uncontrollable and persistent idea, thought, image, or emotion, and the person cannot help thinking even though it creates significant distress or anxiety. Disorders that comprise a compulsion are those that include a repetitive, excessive, meaningless activity or mental exercise that a person performs in an attempt to avoid distress or worry.

Obsessions relate to problems that most people would consider far removed from normal, daily events and concerns. In some embodiments, obsessions can include fears, worries, persistent doubts, scary images, and sexual images. For example, obsessions may include, but are not limited to, fear of contamination as from doorknobs or handshakes, worry about leaving things in their proper order, persistent doubts about one's responsible behavior, scary images involving violent acts, and persistent images of sexual acts. In some embodiments, people with obsessions may find themselves acting in compulsive ways, in largely futile attempts, to relieve the anxiety associated with their persistent, unpleasant thoughts. Others suffering from obsessions may be constantly pre-occupied in the exercise of trying to control or ignore them.

In some embodiments, compulsions are not "voluntary" activities and, thus, are not performed for pleasure, but rather, the person with a compulsion feels the need to engage in a particular behavior to relieve the stress and discomfort which would become overwhelming if the activity were not performed in a specific, repeated manner. Examples of compulsive motor activities include, but are not limited to, washing hands, repeatedly checking the security of a locked door, and arranging and rearranging items in a set order. Some examples of compulsory mental acts are counting or silently repeating specific words. If a person troubled by compulsions is unable to perform such activities, stress and discomfort increase. In some embodiments, compulsions are attempts to undo obsessions and are usually not successful.

The Quick Reference to the diagnostic criteria from DSM-IV-TR (2000) states six characteristics of obsessions and compulsions. Obsessions can include (1) recurrent and persistent thoughts, impulses, or images that are experienced as intrusive and that cause marked anxiety or distress; (2) the thoughts, impulses, or images are not simply excessive worries about real-life problems; (3) the person attempts to ignore or suppress such thoughts, impulses, or images, or to neutralize them with some other thought or action; (4) the person recognizes that the obsessional thoughts, impulses, or images are a product of his or her own mind, and are not based in reality. Compulsions can include (1) repetitive behaviors or mental acts that the person feels driven to perform in response to an obsession, or according to rules that must be applied rigidly; and (2) the behaviors or mental acts are aimed at preventing or reducing distress or preventing some dreaded event or situation; however, these behaviors or mental acts are not actually connected to the issue, or they are excessive.

Obsessive-compulsive disorder (OCD) is an example of a disorder that can be treated by the methods taught herein. To be diagnosed with OCD, a person has either obsessions or compulsions alone, or obsessions and compulsions. In some embodiments, the subject having OCD may be diagnosed with a related condition, where the subject was misproperly diagnosed as having OCD and has only the related condition, the subject has only the related condition, or the subject has both the OCD and the related condition. In some embodiments, for example, a subject having OCD may be diagnosed with a generalized anxiety disorder, anorexia nervosa, social anxiety disorder, bulimia nervosa, Tourette syndrome, Asperger syndrome, compulsive skin picking, body dysmorphic disorder, trichotillomania, or an obsessive-compulsive personality disorder. In some embodiments, the subject having OCD may also be diagnosed as having a drug addiction. In some embodiments, the subject having OCD may also be diagnosed as suffering from panic attacks. In some embodiments, a drug addiction in the subject having OCD serves as a type of compulsive behavior and not just as a coping mechanism. In some embodiments, the subject having OCD may also be diagnosed as having depression.

In some embodiments, the method can be used in the treatment of an immune disorder such as, for example, disorders that include immunodeficiencies, autoimmunity, or hypersensitivities. Immunodeficiency diseases can occur when the immune system is less active than normal, resulting in recurring and life-threatening infections. In some embodiments, immunodeficiencies can either be the result of a genetic disease, such as severe combined immunodeficiency, or be produced by pharmaceuticals or an infection, such as the acquired immune deficiency syndrome (AIDS) that is caused by the retrovirus HIV. Autoimmune diseases can result from a hyperactive immune system attacking normal tissues as if they were foreign organisms. In some embodiments, the autoimmune diseases can include, but are not limited to, rheumatoid arthritis, diabetes mellitus type 1, and lupus erythematosus. Other disorders include chronic fatigue syndrome, chronic fatigue immunodeficiency syndrome, and immediate hypersensitivies. Moreover, since another important role of the immune system is to identify and eliminate tumors, the methods taught herein are contemplated for use in the treatment of cancers.

In some embodiments, the method can be used in the treatment of a neurodegenerative disorder. Neurodegenerative diseases, for example, can result from deterioration of neurons or demyelination, which leads to dysfunctions and disabilities. Neurodegenerative disorders are crudely divided into two groups, not mutually exclusive, according to phenotypic effects and include, for example, (1) conditions causing problems with movements, such as ataxia, and (2) conditions affecting memory and related to dementia. Examples of neurodegenerative disorders include, but are not limited to, demyelinating disorders, such as multiple sclerosis; Parkinson's Disease; and Alzheimer's Disease. In some embodiments, for example, the method can be used in the treatment of amyotrophic lateral sclerosis or fibromyalgia.

The formulations can also be administered alone, in some embodiments, such that only the serotonergic agent or the dopaminergic agent is titrated to an endpoint. The teachings are also directed to a method of using one of the formulations for remitting a deficiency in a neurotransmitter level in a subject through a taste titration. The method comprises orally administering a serotonergic agent or a dopaminergic agent in a formulation. The serotonergic agent or the dopaminergic agent can be delivered to the subject oral transmucosally. The formulation further comprises a flavoring agent and a carrier base. The flavoring agent can function as a taste indicator of the endpoint of a taste titration of the serotonergic or dopaminergic agent for a subject receiving an oral administration of the formulation, and the endpoint is indicated to the subject by a change in the intensity of the flavor of the flavoring agent. The next step includes ceasing the administering of the formulation at the endpoint. The serotonergic formulation and the dopaminergic formulation function together to remit deficiencies and imbalances in the subject's serotonin and dopamine levels.

In some embodiments, the serotonergic agent can be titrated to a subject having a serotonin deficit. There are many known functions of serotonin including, but not limited to, control of appetite, sleep, memory and learning, temperature regulation, mood, behavior (including sexual and hallucinogenic behavior), cardiovascular function, muscle contraction, endocrine regulation, and depression. In some embodiments, the serotonergic agent can be administered using the methods taught herein as a treatment for depression. In some embodiments, the serotonergic agent can be administered using the methods taught herein as a treatment for weight loss, depression, anxiety, nerves, headache, and ADD. In some embodiments, the serotonergic agent can be administered using the methods taught herein as a treatment for patients with chronic pain, cocaine addiction, and other chemical dependencies, attention disorders, anxiety, Alzheimer's dementia, fibromyalgia, insomnia, and migraines.

In some embodiments, the dopaminergic agent can be titrated to a subject having a dopamine deficit. Dopamine has many functions in the brain including, but not limited to, roles in behavior and cognition, motor activity, motivation and reward, inhibition of prolactin production, sleep, mood, attention and learning. In some embodiments, the dopaminergic agent can be administered using the methods taught herein as a treatment for Parkinson's disease, since it is known that patients with Parkinson's lack dopamine and when supplemented benefit from symptom relief. In some embodiments, the dopaminergic agent can be administered using the methods taught herein as a treatment for in attention-deficit-hyperactivity disorder. In some embodiments, the dopaminergic agent can be administered using the methods taught herein as a treatment for depression and, in some embodiments, as a treatment for nicotine addiction to assist in smoking cessation.

In some embodiments, the formulations and systems discussed above can be in the form of kits, whereby the kits comprise one or both of the formulations. The kits may contain devices to assist in the titrations, such as syringes or droppers, as well as instructions for use. In some embodiments, the instructions will provide contraindications and other useful information. For example, infrequently, there is a treatable first-dose phenomenon, wherein the administration of an agent can cause a precipitous reaction associated with a host of symptoms that include sudden onset of shortness of breath, nausea, flushing, lightheadedness, or mental confusion. A small dose of the correct suspension will typically disperse the undesired symptoms. Prior to starting the first dose administration of a combination of a serotonin precursor or dopamine precursor using the method taught herein, a large drop of each suspension can be placed on a nonabsorbent substance such as a piece of glass. Should a first-dose response occur, immediately have the patient dip a finger into one of the suspensions and test taste it. If pleasant, continue administering that suspension. If unpleasant, administer the other suspension. Once the symptoms are alleviated, continue with the titration as described in the methods taught herein.

Without intending to be limited to any theory or mechanism of action, the following examples are provided to further illustrate the teachings presented herein. It should be appreciated that there are several variations contemplated within the skill in the art, and that the examples are not intended to be construed as providing limitations to the claims.

EXAMPLE 1

Preparation of a 5-hydroxytryptophan (5-HTP) Suspension

A 5-hydroxytryptophan suspension was prepared at a concentration of 1.25 mg 5-HTP/gtt. 0.9 g of a 5-HTP powder, 0.025 g of STEVIA ext powder, and 0.06 g of xanthan gum powder was weighed and triturated with a sufficient quantity of propylene glycol to make a smooth paste. A drop of blue food coloring was added and mixed with a sufficient quantity of ORA-SWEET to make 30 ml of the formulation.

The formulation was placed in a 1 oz amber glass boston round bottle having a dropper cap with a calibrated curved glass pipette for administration. The formulation was marked "refrigerate and shake well before use".

Two strengths of the 5-HTP suspension were made and used in taste titrations, 1.25 mg/gtt and 2.5 mg/gtt, by simply doubling the amount of 5-HTP in the preparation method.

EXAMPLE 2

Preparation of a Levodopa Suspension

A levodopa suspension was prepared at a concentration of 3.33 mg levodopa/gtt. 3.0 g of a levodopa powder, 1.0 g of a micronized silica gel powder, 0.06 g of butylated hydroxytoluene fcc crystals, and 0.12 g of saccharin insoluble powder was weighed. 0.02 g of an orange food color was weighed and mixed with some of the levodopa powder to make the color smooth in the base mixture. The remainder of the levodopa and the saccharine insoluble powder was then added to the base mixture. The butylated hyddroxytoluene fcc crystals were ground and added to a small amount of Base g (sweet almond oil). The micronized silica gel was slowly triturated into the base mixture until smooth, and all of the ingredients were combined with mixing until all was smooth and almond oil was added in a sufficient quantity to make 30 ml of the formulation.

The formulation was placed in a 1 oz amber glass boston round bottle having a dropper cap with a calibrated curved glass pipette for administration. The formulation was marked "refrigerate and shake well before use".

Three strengths of the levodopa suspension were made and used in taste titrations, 3.0 mg/gtt, 6.0 mg/gtt, and 12.0 mg/gtt, by simply doubling and quadrupling the amount of levodopa in the preparation method.

EXAMPLE 3

Administering the 5-hydroxytryptophan and Levodopa Suspensions

Take a careful history of the patient to identify contraindications, which include, but are not limited to, MAO inhibitors, pregnancy, or the possibility of a pheochromocytoma or carcinoid syndrome. The suspensions are administered in vials, and the levodopa vials should be tinted. The screw top of each vial can include a dropper for administration. The 5-HTP suspension is stable at room temperature, but the levodopa suspension is subject to oxidation and must be kept refrigerated.

Shake the suspension before use. Draw either the 5-HTP suspension or the levodopa suspension into the dropper, as a first suspension, and instruct the patient to administer a single drop to the tongue and report its taste. The patient will almost always report a pleasant taste, such as "refreshing" regarding the 5-HTP, or "tangerine", "orange", or "citrusey" regarding the levodopa. The patient is instructed under supervision to continue administering the first suspension until the flavor becomes attenuated. When the flavor becomes neutral, and loses flavor at a bland endpoint of the titration, the patient is instructed to repeat the process with the other monoamine precursor, as a second suspension, to the bland endpoint of the titration of the second suspension.

The cycle can be repeated, if necessary, to ensure that there is a balance of the neurotransmitter levels in the patient's body. The patient is instructed to return to the first suspension, which may again be pleasant to taste, and to repeat the titration to blandness. The second suspension is also titrated again until blandness, and the process is repeated until the first drop of either suspension is bland. It has been found that the need for more than one titration cycle is rare after the first administration of the two suspensions.

Should either suspension be administered beyond the recommended endpoint, the suspension becomes increasingly dysgeusic; nausea and then vomiting follows. The treatment for suspension-induced nausea is the immediate administration of the other suspension which can promptly alleviate these symptoms.

The suspensions can be administered twice per day, or when the patient notices that the primary symptoms are returning. It has been found that the administrations are rarely needed more than 2-3 times per day, and the dose is frequently standardized and easy for the patient to administer.

EXAMPLE 4

Treating Craving in Alcohol and Cocaine Addiction with the 5-hydroxytryptophan and Levodopa Suspensions A 46 year old male with a history of a combined cocaine and alcohol abuse presented himself for treatment. He was noted to be in acute alcohol withdrawal with hypertension, tachycardia and tremors. A self-administered psychometric test (SCL-90) was abnormal with depressive and anxiety scores having more than 2 standard deviations above normal. During his pre-treatment interview, the patient stated he was acutely depressed and anxious. Cocaine and alcohol craving was severe.

The treatment was initiated. Titration with 1.5 mg/gtt 5-HTP proceeded until the patient reported that the suspension tasted bland. 22.5 mg of 5-HTP had been administered. This was followed by titrating with 3.33 mg/gtt levodopa until the patient reported that the suspension tasted bland. Approximately 20 mg of levodopa had been administered before the patient reported loss of taste and sweetness.

The patient's status was re-evaluated. The patient's vital signs were normal and his tremor had abated. The patient denied any further alcohol or cocaine craving, and both his depression and anxiety had abated.

The patient left the office with prescriptions for a formulation containing 2.5 mg/gtt 5-HTP and 6.66 mg/gtt levodopa for self treatment using the titration method. The patient returned in two weeks and reported no alcohol or cocaine use. Any cravings had remitted with the use of the treatment. A repeat psychometric test was normal. Repeat visits at 2 and 6 months were similar in nature.

EXAMPLE 5

Treating Methamphetamine Addiction with the 5-hydroxytryptophan and Levodopa Suspensions A 24 year old white male had been suffering from methamphetamine addiction for two years and was acutely craving methamphetamines at the first visit.

Titration with 1.5 mg/gtt 5-HTP proceeded until the patient reported that the suspension tasted bland. 40.0 mg of 5-HTP had been administered. This was followed by titrating with 3.33 mg/gtt levodopa until the patient reported that the suspension tasted bland. Approximately 45 mg of levodopa had been administered before the patient reported loss of taste and sweetness. After treatment, the patient denied any further cravings.

The patient left the office with prescriptions for a formulation containing 2.5 mg/gtt 5-HTP and 6.66 mg/gtt levodopa for self treatment using the titration method. The patient returned in two weeks and reported no alcohol or cocaine use. Any cravings had remitted with the use of the treatment. A repeat psychometric test was normal.

EXAMPLE 6

Treating Amytrophic Lateral Sclerosis with the 5-hydroxytryptophan and Levodopa Suspensions A 52 year old male had rapidly progressive bulbar amyotrophic lateral sclerosis for ten months. Upon examination, he had uncontrollable drooling and speech that was unintelligible to all but his "translator," which was his niece. Under his physician's care he used the taste titration of both levodopa and 5-HTP.

Within 15 minutes, the patient's drooling had abated to the point that he no longer clutched an absorbent pad to his mouth. His speech had so remarkably improved that he was able to converse readily with all in the office. He was obviously overjoyed and walked around with a portable recorder.

After several hours of observation, the patient's speech began to deteriorate. The patient titrated the formulations without physician supervision and, this time, his speech nearly instantaneously remitted in a similar fashion.

EXAMPLE 7

Treating Cravings for Marijuana with the 5-hydroxytryptophan and Levodopa Suspensions A 60 year old male craved marijuana and had associated conditions of Hepatitis C at a viral load of 1.5M, depression, repressed hostility, and obesity. Hepatitis and fibrosis are associated the type-2 T-helper cell excess.

The patient received 5-HTP and levodopa using the titration method and self-administered the formulations twice a day after the initial visit. Two weeks after the initial visit, the cravings for marijuana were totally absent.

The patient connected marijuana use with working in that he would lock his door and smoke marijuana for days to offset cravings for marijuana created by the stress of the work environment. The patient no longer felt this need and craving to smoke marijuana to offset stress, was very excited about the treatment and referred friends and family for the treatment.

The patient also realized a reduction in cravings for food, stating that before treatment he never reached satiety for food and is now able to recognize when hunger is abated.

The patient self-administered the treatment for three weeks and returned for another assessment. The patient still did not suffer marijuana cravings and continued to lose weight.

EXAMPLE 8

Treating the Addictions of Multiple Patients to Alcohol and Cocaine with the 5-hydroxytryptophan and Levodopa Suspensions Three patients used the taste titration treatment taught herein. Two patients had an addiction to alcohol and one patient had an addiction to cocaine. In each case, the patients reported that the cravings immediately dissipated. The overseeing doctor also reported that in each case, the normal withdrawal symptoms immediately ceased.

Another patient began the treatment to help with his alcohol addiction. While he reported immediate results in the decreasing of his craving for alcohol, it was also surprising to him was that his depression went away.

Another patient suffered depression and was addicted to alcohol, complaining that he was not in a normal functional state. He stated that would drink a fifth of whiskey every day. As he used the treatment, the desire for alcohol returned to normal and his depression decreased, and he noted that he returned to what he felt was a normal functional state.

EXAMPLE 9

Treating Depression with the 5-hydroxytryptophan and Levodopa Suspensions and the Effect of Exercise A patient who was depressed was using the taste titration treatment taught herein. He had found a dose that worked well for him, and the dose did not change over a couple weeks of administration. The patient felt better and decided to begin jogging. After his first jog, he administered the titration and found that he needed exactly one half of the 5-HTP that he had been administering. The exercise increased his serotonin level, proving that needed doses can change based on life changes. After continued administration and life changes, the patient ceased taking the treatment and there was no relapse of the depression.

EXAMPLE 10

Treating Depression with the 5-hydroxytryptophan and Levodopa Suspensions and the Effect of Exercise A student with ADD was frustrated with his academic performance. After administration of the treatment, the student reported that it is easier for him to concentrate, and he is gets better grades when he is on this treatment.

One of skill reading the teachings will appreciate that the concepts can extend into additional embodiments that go well-beyond a literal reading of the claims, the inventions recited by the claims, and the terms recited in the claims.

I claim:

1. A system for use in balancing neurotransmitter levels in a subject through a taste titration, the system comprising:
    a serotonergic formulation comprising a serotonergic agent, a first flavoring agent, and a first carrier base; wherein, the first flavoring agent functions as a taste indicator of a serotonergic endpoint of a taste titration of the serotonergic agent for the subject receiving the serotonergic formulation, the serotonergic endpoint indicated to the subject by a change in the flavor of the first flavoring agent, and functioning to remit a deficiency in the subject's serotonin level through a delivery of the serotonergic agent across a blood brain barrier;
    a dopaminergic formulation comprising a dopaminergic agent, a second flavoring agent, and a second carrier base; wherein, the second flavoring agent functions as a taste indicator of a dopaminergic endpoint of the taste titration of the dopaminergic agent for the subject receiving the dopaminergic formulation, the dopaminergic endpoint indicated to the subject by a change in the flavor of the second flavoring agent, and functioning to remit a deficiency in the subject's dopamine level through a delivery of the dopaminergic agent across the blood brain barrier; and
    a titration means for facilitating a gradual oral transmucosal delivery of the serotonergic agent or dopaminergic agent to the subject to the serotonergic endpoint or dopaminergic endpoint;
    wherein, the serotonergic formulation and the dopaminergic formulation function together to remit deficiencies and imbalances in the subject's serotonin and dopamine levels, and the serotonergic endpoint and dopaminergic endpoint indicate an amount of the serotonergic formulation and an amount of the dopaminergic formulation that provides a desired response in the subject using the oral transmucosal delivery while mitigating risk of overdose.

2. The system of claim 1, wherein the serotonergic agent or the dopaminergic agent comprises a hydroxylated aromatic acid monoamine precursor to serotonin or dopamine.

3. The system of claim 1, wherein the serotonergic agent comprises 5-hydroxytryptophan.

4. The system of claim 1, wherein the dopaminergic agent comprises levodopa.

5. The system of claim 1, wherein the flavor of the serotonergic formulation or dopaminergic formulation changes from sweet to bitter.

6. The system of claim 1, wherein the first flavoring agent or the second flavoring agent comprises a sweetening agent.

7. The system of claim 1, wherein the serotonergic agent or the dopaminergic agent has a flavor that (i) is at least substantially unnoticed by the subject at the start of the titration and (ii) becomes at least substantially noticed by the subject at the end of the titration.

8. The system of claim 1, wherein the flavor at the serotonergic endpoint is bitter.

9. The system of claim 1, wherein the flavor at the dopaminergic endpoint bitter.

10. The system of claim 1, wherein the serotonergic formulation or the dopaminergic formulation is in the form of a liquid for administering to the subject's tongue or oral mucosa.

11. The system of claim 1, wherein the serotonergic formulation or the dopaminergic formulation in the form of a solid for administering to the subject's tongue or oral mucosa.

12. The system of claim 1, wherein the serotonergic formulation or the dopaminergic formulation is in the form of a lozenge for administering to the subject's tongue or oral mucosa, such that the lozenge functions to perform the titration through an oral dissolution of the lozenge in the subject.

13. The system of claim 1, wherein the serotonergic agent contains a first coloring agent and the dopaminergic agent contains a second coloring agent, wherein the color of the first coloring agent and the color of the second coloring are distinguishable to the subject.

14. A method for balancing neurotransmitter levels in a subject through a taste titration using the system of claim 1, the method comprising:
a titration component or means for orally administering the serotonergic formulation comprising the serotonergic agent, the first flavoring agent, and the first carrier base to the serotonergic endpoint of a taste titration of the serotonergic formulation, the administering of the serotonergic formulation functioning to remit a deficiency in the subject's serotonin level; wherein, the first flavoring agent functions as the taste indicator of the serotonergic endpoint for the subject receiving the serotonergic formulation, the serotonergic endpoint is identified by the change in the flavor of the first flavoring agent to the subject, and the serotonergic agent is delivered to the subject oral transmucosally; and,
ceasing the administering of the serotonergic formulation at the serotonergic endpoint; and,
a titration component or means for orally administering the dopaminergic formulation comprising the dopaminergic agent, the second flavoring agent, and the second carrier base to the dopaminergic endpoint of the taste titration of the dopaminergic formulation, the administering of the dopaminergic formulation functioning to remit a deficiency in the subject's dopamine level; wherein, the second flavoring agent functions as the taste indicator of the dopaminergic endpoint for the subject receiving the dopaminergic formulation, wherein the dopaminergic endpoint is identified by the change in the intensity of the flavor of the second flavoring agent to the subject, and the dopaminergic agent is delivered to the subject oral transmucosally; and,
ceasing the administering of the dopaminergic agent formulation at the dopaminergic endpoint;
wherein, the serotonergic formulation and the dopaminergic formulation function together to remit deficiencies and imbalances in the subject's serotonin and dopamine levels, and the serotonergic endpoint and dopaminergic endpoint indicate an amount of the serotonergic formulation and an amount of the dopaminergic formulation that provides a desired response in the subject.

15. The method of claim 14, wherein the titration includes orally administering the serotonergic formulation or the dopaminergic formulation in the form of a liquid to the subject's tongue or oral mucosa and ceasing administration at the endpoint.

16. The method of claim 14, wherein the titration includes orally administering the serotonergic formulation or the dopaminergic formulation in the form of a solid to the subject's tongue or oral mucosa and ceasing administration at the endpoint.

17. The method of claim 14, wherein the titration includes orally administering the serotonergic formulation or the dopaminergic formulation in the form of a lozenge to the subject's tongue or oral mucosa and ceasing administration at the endpoint, such that the lozenge function to perform the titration through an oral dissolution of the lozenge in the subject.

18. The method of claim 14, wherein the serotonergic agent or the dopaminergic agent comprises a hydroxylated aromatic acid monoamine precursor.

19. The method of claim 14, wherein the serotonergic agent comprises 5-hydroxytryptophan.

20. The method of claim 14, wherein the dopaminergic agent comprises levodopa.

21. The method of claim 14, wherein the flavor of the serotonergic formulation or dopaminergic formulation changes from sweet to bitter.

22. The method of claim 14, wherein the first flavoring agent or the second flavoring agent comprises a sweetening agent.

23. The method of claim 14, wherein the serotonergic formulation or the dopaminergic formulation has a flavor that (i) is at least substantially unnoticed by the subject at the start of the titration and (ii) becomes at least substantially noticed by the subject at the end of the titration.

24. The method of claim 14, wherein the flavor at the serotonergic endpoint or the dopaminergic endpoint is bitter.

25. The method of claim 14, wherein the method is used to ameliorate cravings in the treatment of an addictive disorder.

26. The method of claim 14, wherein the method is used to ameliorate withdrawal symptoms in the treatment of an addictive disorder.

27. The method of claim 14, wherein the method is used in the treatment of an affective disorder.

28. The method of claim 14, wherein the method is used in the treatment of an obsessive or compulsive disorder.

29. The method of claim 14, wherein the method is used in the treatment of an autoimmune disorder.

30. The method of claim 14, wherein the method is used in the treatment of an immune disorder.

31. The method of claim 14, wherein the method is used in the treatment of a neurodegenerative disorder.

32. The method of claim 14, wherein the method is used in the treatment of amyotrophic lateral sclerosis.

33. The method of claim 14, wherein the method is used in the treatment of fibromyalgia.

34. The system of claim 1, wherein the titration means facilitates administration of the serotonergic formulation or the dopaminergic formulation in the form of liquid drops.

35. The system of claim 1, wherein the titration means facilitates administration of the serotonergic agent or the dopaminergic agent oral transmucosally through the form of a gradual oral delivery of a solution.

36. The system of claim 1, wherein the titration means facilitates administration of the serotonergic agent or the dopaminergic agent oral transmucosally through the form of a gradual oral delivery of a suspension.

37. The system of claim 1, wherein the titration means facilitates administration of the serotonergic agent or the dopaminergic agent oral transmucosally through the form of a gradual oral delivery of an emulsion.

38. The system of claim 1, wherein the titration means facilitates administration of the serotonergic formulation or the dopaminergic formulation in the form of solid particles.

39. The system of claim 1, wherein the titration means facilitates administration of the serotonergic agent or the dopaminergic agent oral transmucosally through the form of a gradual oral delivery of a granule.

40. The system of claim 1, wherein the titration means facilitates administration of the serotonergic agent or the dopaminergic agent oral transmucosally through the form of a gradual oral delivery of a powder.

41. A system for use in balancing neurotransmitter levels in a subject through a taste titration, the system comprising:
   a serotonergic formulation comprising a serotonergic agent, a first flavoring agent, and a first carrier base; wherein, the first flavoring agent functions as a taste indicator of a serotonergic endpoint of a taste titration of the serotonergic agent for the subject receiving the serotonergic formulation, the serotonergic endpoint indicated to the subject by a change in the flavor of the first flavoring agent, and functioning to remit a deficiency in the subject's serotonin level through a delivery of the serotonergic agent across a blood brain barrier;
   a dopaminergic formulation comprising a dopaminergic agent, a second flavoring agent, and a second carrier base; wherein, the second flavoring agent functions as a taste indicator of a dopaminergic endpoint of the taste titration of the dopaminergic agent for the subject receiving the dopaminergic formulation, the dopaminergic endpoint indicated to the subject by a change in the flavor of the second flavoring agent, and functioning to remit a deficiency in the subject's dopamine level through a delivery of the dopaminergic agent across the blood brain barrier; and
   a titration component for facilitating a gradual oral transmucosal delivery of the serotonergic agent or dopaminergic agent to the subject to the serotonergic endpoint or dopaminergic endpoint;
   wherein, the serotonergic formulation and the dopaminergic formulation function together to remit deficiencies and imbalances in the subject's serotonin and dopamine levels, and the serotonergic endpoint and dopaminergic endpoint indicate an amount of the serotonergic formulation and an amount of the dopaminergic formulation that provides a desired response in the subject using the oral transmucosal delivery while mitigating risk of overdose.

42. The system of claim 41, wherein the titration component facilitates administration of the serotonergic formulation or the dopaminergic formulation in the form of liquid drops.

43. The system of claim 41, wherein the titration component facilitates administration of the serotonergic agent or the dopaminergic agent oral transmucosally through the form of a gradual oral delivery of a solution.

44. The system of claim 41, wherein the titration component facilitates administration of the serotonergic agent or the dopaminergic agent oral transmucosally through the form of a gradual oral delivery of a suspension.

45. The system of claim 41, wherein the titration component facilitates administration of the serotonergic agent or the dopaminergic agent oral transmucosally through the form of a gradual oral delivery of an emulsion.

46. The system of claim 41, wherein the titration component facilitates administration of the serotonergic formulation or the dopaminergic formulation in the form of solid particles.

47. The system of claim 41, wherein the titration component facilitates administration of the serotonergic agent or the dopaminergic agent oral transmucosally through the form of a gradual oral delivery of a granule.

48. The system of claim 41, wherein the titration component facilitates administration of the serotonergic agent or the dopaminergic agent oral transmucosally through the form of a gradual oral delivery of a powder.

49. The system of claim 41, wherein the serotonergic agent or the dopaminergic agent comprises a hydroxylated aromatic acid monoamine precursor to serotonin or dopamine.

50. The system of claim 41, wherein the serotonergic agent comprises 5-hydroxytryptophan.

51. The system of claim 41, wherein the dopaminergic agent comprises levodopa.

52. The system of claim 41, wherein the serotonergic agent or the dopaminergic agent has a flavor that (i) is at least substantially unnoticed by the subject at the start of the titration and (ii) becomes at least substantially noticed by the subject at the end of the titration.

53. The system of claim 41, wherein the flavor at the serotonergic endpoint or the dopaminergic endpoint is bitter.

54. The system of claim 41, wherein the serotonergic formulation or the dopaminergic formulation is in the form of a lozenge for administering to the subject's tongue or oral mucosa, such that the lozenge functions to perform the titration through an oral dissolution of the lozenge in the subject.

\* \* \* \* \*